(12) United States Patent
Lynch et al.

(10) Patent No.: US 6,827,700 B2
(45) Date of Patent: *Dec. 7, 2004

(54) SHUNT DEVICE AND METHOD FOR TREATING GLAUCOMA

(75) Inventors: Mary G. Lynch, Atlanta, GA (US); Reay H. Brown, Atlanta, GA (US)

(73) Assignee: GMP Vision Solutions, Inc., Ft. Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/445,740

(22) Filed: May 27, 2003

(65) Prior Publication Data

US 2003/0220603 A1 Nov. 27, 2003

Related U.S. Application Data

(63) Continuation of application No. 10/242,385, filed on Sep. 12, 2002, now Pat. No. 6,626,858, which is a continuation of application No. 09/558,505, filed on Apr. 26, 2000, now Pat. No. 6,450,984
(60) Provisional application No. 60/131,030, filed on Apr. 26, 1999.

(51) Int. Cl.[7] ............................................... A61M 5/00
(52) U.S. Cl. .......................................... 604/8; 604/284
(58) Field of Search ............................ 604/8, 264, 284, 604/523; 606/107; 623/4.1, 1.1, 11.11, 1.35

(56) References Cited

U.S. PATENT DOCUMENTS

| | | |
|---|---|---|
| 3,159,161 A | 12/1964 | Ness |
| 3,788,327 A | 1/1974 | Donowitz et al. .......... 128/350 |
| 4,037,604 A | 7/1977 | Newkirk ..................... 128/350 |
| 4,175,563 A | 11/1979 | Arenberg et al. ........... 128/350 |
| 4,402,681 A | 9/1983 | Haas et al. ..................... 604/9 |
| 4,428,746 A | 1/1984 | Mendez .......................... 604/8 |

(List continued on next page.)

FOREIGN PATENT DOCUMENTS

| | | | | |
|---|---|---|---|---|
| AU | 200072059 | 7/2001 | | |
| CA | 2244646 | 2/1999 | | |
| CH | 92111244 | 7/1993 | | |
| DE | 198 40 047 | 3/2000 | | |
| DE | 19840047 A1 | * 3/2000 | ............. | A61F/2/14 |
| EP | 0 881 055 | 2/1998 | | |
| EP | 0 858 788 | 8/1998 | | |
| EP | 0 898 947 | 3/1999 | | |
| EP | 1114627 | 7/2001 | | |
| FR | 2710269 | 3/1995 | | |
| JP | 11123205 | 5/1999 | | |
| WO | 89/00869 | 2/1989 | | |
| WO | 92/00112 | 1/1992 | | |
| WO | 92/19294 | 11/1992 | | |
| WO | 96/36377 | 11/1996 | | |
| WO | 98/23237 | 6/1998 | | |
| WO | 98/30181 | 7/1998 | | |
| WO | 98/35639 | 8/1998 | | |
| WO | 99/26567 | 6/1999 | | |
| WO | 99/30641 | 6/1999 | | |
| WO | 99/38470 | 8/1999 | | |
| WO | 00/13627 | 3/2000 | | |
| WO | 00/64389 | 11/2000 | | |

OTHER PUBLICATIONS

Allen D. Beck and Mary G. Lynch, "360° Trabeculotomy for Primary Congenital Glaucoma," *Arch. Ophthalmol.* 113 (Sep. 1995), pp. 1200–1202.

(List continued on next page.)

*Primary Examiner*—Edward K. Look
*Assistant Examiner*—Richard A Edgar
(74) *Attorney, Agent, or Firm*—Sutherland Asbill & Brennan LLP (57) ABSTRACT

Shunt devices and a method for continuously decompressing elevated intraocular pressure in eyes affected by glaucoma by diverting excess aqueous humor from the anterior chamber of the eye into Schlemm's canal where post-operative patency can be maintained with an indwelling shunt device which surgically connects the canal with the anterior chamber. The shunt devices provide uni- or bi-directional flow of aqueous humor into Schlemm's canal.

47 Claims, 6 Drawing Sheets

U.S. PATENT DOCUMENTS

| | | |
|---|---|---|
| 4,457,757 A | 7/1984 | Molteno ............... 604/294 |
| 4,501,274 A | 2/1985 | Skjaerpe ............... 128/305 |
| 4,521,210 A | 6/1985 | Wong ............... 604/8 |
| 4,554,918 A | 11/1985 | White ............... 604/10 |
| 4,604,087 A | 8/1986 | Joseph ............... 604/9 |
| 4,632,842 A | 12/1986 | Karwoski et al. ............... 427/2 |
| 4,634,418 A | 1/1987 | Binder ............... 604/8 |
| 4,718,907 A | 1/1988 | Karwoski et al. ............... 623/12 |
| 4,733,665 A | 3/1988 | Palmaz ............... 128/343 |
| 4,750,901 A | 6/1988 | Molteno ............... 604/8 |
| 4,787,885 A | 11/1988 | Binder ............... 604/8 |
| 4,846,172 A | 7/1989 | Berlin ............... 128/303.1 |
| 4,863,457 A | 9/1989 | Lee ............... 604/891 |
| 4,886,488 A | 12/1989 | White ............... 604/9 |
| 4,900,300 A | 2/1990 | Lee ............... 604/22 |
| 4,936,825 A | 6/1990 | Ungerleider ............... 604/8 |
| 4,946,436 A | 8/1990 | Smith ............... 604/8 |
| 4,968,296 A | 11/1990 | Ritch et al. ............... 604/8 |
| 5,041,081 A | 8/1991 | Odrich ............... 604/9 |
| 5,073,163 A | 12/1991 | Lippman ............... 604/9 |
| 5,092,837 A | 3/1992 | Ritch et al. ............... 604/8 |
| 5,095,887 A | 3/1992 | Leon et al. ............... 128/4 |
| 5,127,901 A | 7/1992 | Odrich ............... 604/9 |
| 5,129,895 A | 7/1992 | Vassiliadis et al. ............... 606/6 |
| 5,171,213 A | 12/1992 | Price, Jr. ............... 604/9 |
| 5,178,604 A | 1/1993 | Baerveldt et al. ............... 604/8 |
| 5,180,362 A | 1/1993 | Worst ............... 604/8 |
| 5,246,451 A | 9/1993 | Trescony et al. ............... 623/1 |
| 5,300,020 A | 4/1994 | L'Esperance, Jr. ............... 604/9 |
| 5,318,513 A | 6/1994 | Leib et al. ............... 604/8 |
| 5,334,137 A | 8/1994 | Freeman ............... 604/8 |
| 5,338,291 A | 8/1994 | Speckman et al. ............... 604/9 |
| 5,346,464 A | 9/1994 | Camras ............... 604/9 |
| 5,360,399 A | 11/1994 | Stegmann ............... 604/49 |
| 5,370,607 A | 12/1994 | Memmen ............... 604/8 |
| 5,370,641 A | 12/1994 | O'Donnell, Jr. ............... 606/4 |
| 5,372,577 A | 12/1994 | Ungerleider ............... 604/8 |
| 5,397,300 A | 3/1995 | Baerveldt et al. ............... 604/8 |
| 5,433,701 A | 7/1995 | Rubinstein ............... 604/8 |
| 5,454,796 A | 10/1995 | Krupin ............... 604/294 |
| 5,476,445 A | 12/1995 | Baerveldt et al. ............... 604/8 |
| 5,486,165 A | 1/1996 | Stegmann ............... 609/294 |
| 5,520,631 A | 5/1996 | Nordquist et al. ............... 604/8 |
| 5,557,453 A | 9/1996 | Schalz et al. ............... 359/376 |
| 5,558,629 A | 9/1996 | Baerveldt et al. ............... 609/8 |
| 5,558,630 A | 9/1996 | Fisher ............... 604/8 |
| RE35,390 E | 12/1996 | Smith ............... 604/8 |
| 5,601,094 A | 2/1997 | Reiss ............... 128/899 |
| 5,601,549 A | 2/1997 | Miyagi ............... 606/4 |
| 5,626,558 A | 5/1997 | Suson ............... 604/8 |
| 5,626,559 A | 5/1997 | Solomon ............... 604/9 |
| 5,639,278 A | 6/1997 | Dereume et al. ............... 623/1 |
| 5,651,783 A | 7/1997 | Reynard ............... 606/4 |
| 5,670,161 A | 9/1997 | Healy et al. ............... 424/426 |
| 5,676,679 A | 10/1997 | Simon et al. ............... 606/170 |
| 5,681,275 A | 10/1997 | Ahmed ............... 604/9 |
| 5,702,414 A | 12/1997 | Richter et al. ............... 606/166 |
| 5,702,419 A | 12/1997 | Berry et al. ............... 606/198 |
| 5,704,907 A | 1/1998 | Nordquist et al. ............... 604/8 |
| 5,713,844 A | 2/1998 | Peyman ............... 604/9 |
| 5,723,005 A | 3/1998 | Herrick ............... 623/4 |
| 5,741,333 A | 4/1998 | Frid ............... 623/12 |
| 5,743,868 A | 4/1998 | Brown et al. ............... 604/8 |
| 5,752,928 A | 5/1998 | de Roulhac et al. ............... 604/8 |
| 5,766,243 A | 6/1998 | Christensen et al. ............... 623/4 |
| 5,785,674 A | 7/1998 | Mateen ............... 604/9 |
| 5,807,302 A | 9/1998 | Wandel ............... 604/8 |
| 5,810,870 A | 9/1998 | Myers et al. ............... 606/198 |
| 5,830,171 A | 11/1998 | Wallace ............... 604/8 |
| 5,836,939 A | 11/1998 | Negus et al. ............... 606/11 |
| 5,865,831 A | 2/1999 | Cozean et al. ............... 606/6 |
| 5,868,697 A | 2/1999 | Richter et al. ............... 604/8 |
| 5,879,319 A | 3/1999 | Pynson et al. ............... 604/8 |
| 5,882,327 A | 3/1999 | Jacob ............... 604/8 |
| 5,893,837 A | 4/1999 | Eagles et al. ............... 604/9 |
| 5,968,058 A | 10/1999 | Richter et al. ............... 606/166 |
| 5,981,598 A | 11/1999 | Tatton ............... 514/649 |
| 6,004,302 A | 12/1999 | Brierley ............... 604/264 |
| 6,007,510 A | 12/1999 | Nigam ............... 604/8 |
| 6,007,511 A | 12/1999 | Prywes ............... 604/9 |
| 6,033,434 A | 3/2000 | Borghi ............... 623/1 |
| 6,045,557 A | 4/2000 | White et al. ............... 606/108 |
| 6,050,970 A | 4/2000 | Baerveldt ............... 604/28 |
| 6,059,772 A | 5/2000 | Hsia et al. ............... 606/4 |
| 6,059,812 A | 5/2000 | Clerc et al. ............... 606/198 |
| 6,063,116 A | 5/2000 | Kelleher ............... 623/4 |
| 6,063,396 A | 5/2000 | Kelleher ............... 424/428 |
| 6,071,286 A | 6/2000 | Mawad ............... 606/108 |
| 6,077,299 A | 6/2000 | Adelberg et al. ............... 623/24 |
| 6,102,045 A | 8/2000 | Nordquist et al. ............... 128/898 |
| 6,142,990 A | 11/2000 | Burk ............... 606/6 |
| 6,168,575 B1 | 1/2001 | Soltanpour ............... 604/9 |
| 6,174,305 B1 | 1/2001 | Mikus et al. ............... 604/500 |
| 6,193,656 B1 | 2/2001 | Jeffries et al. ............... 600/398 |
| 6,197,056 B1 | 3/2001 | Schachar ............... 623/4.1 |
| 6,228,873 B1 | 5/2001 | Brandt et al. ............... 514/347 |
| 6,231,597 B1 | 5/2001 | Deem et al. ............... 623/1.12 |
| 6,241,721 B1 | 6/2001 | Cozean et al. ............... 606/6 |
| 6,266,182 B1 | 7/2001 | Morita ............... 359/383 |
| 6,268,398 B1 | 7/2001 | Ghosh et al. ............... 514/634 |
| 6,342,058 B1 | 1/2002 | Portney ............... 606/107 |
| 6,375,642 B1 | 4/2002 | Grieshaber et al. ............... 604/294 |
| 6,450,984 B1 * | 9/2002 | Lynch et al. ............... 604/8 |
| 6,464,724 B1 | 10/2002 | Lynch et al. ............... 623/4.1 |
| 6,494,857 B1 | 12/2002 | Neuhann ............... 604/8 |
| 6,533,768 B1 | 3/2003 | Hill ............... 604/521 |
| 6,626,858 B2 * | 9/2003 | Lynch et al. ............... 604/8 |
| 2002/0013546 A1 | 1/2002 | Grieshaber et al. ............... 604/28 |
| 2002/0026200 A1 | 2/2002 | Savage ............... 606/108 |
| 2002/0072673 A1 | 6/2002 | Yamamoto et al. ............... 600/452 |
| 2002/0082591 A1 | 6/2002 | Haefliger ............... 606/6 |
| 2002/0133168 A1 | 9/2002 | Smedley et al. ............... 606/108 |
| 2002/0143284 A1 | 10/2002 | Tu et al. ............... 604/9 |
| 2002/0165478 A1 | 11/2002 | Gharib et al. ............... 604/8 |
| 2002/0169130 A1 | 11/2002 | Tu et al. ............... 514/12 |
| 2002/0188308 A1 | 12/2002 | Tu et al. ............... 606/167 |

FOREIGN PATENT DOCUMENTS

| | | |
|---|---|---|
| WO | 00/64390 | 11/2000 |
| WO | 00/64391 | 11/2000 |
| WO | 00/64393 | 11/2000 |
| WO | 00/72788 | 12/2000 |
| WO | 01/41685 | 6/2001 |
| WO | 01/50943 | 7/2001 |
| WO | 01/78631 | 10/2001 |
| WO | 01/78656 | 10/2001 |
| WO | 01/97727 | 12/2001 |
| WO | 02/36052 | 5/2002 |
| WO | 02/056758 | 7/2002 |
| WO | 02/074052 | 9/2002 |
| WO | 02/080811 | 10/2002 |

OTHER PUBLICATIONS

Buskirk, E. Michael et al., "Lens Depression and Aqueous Outflow in Enucleated Primate Eyes", American Journal of Ophthalmology, vol. 76, No. 5, Nov. 1973, pp. 632–640.

Buskirk, E. Michael, "Trabeculotomy in the immature, enucleated human eye", Invest. Ophthalmol. Visual Sci., vol. 16, No. 1, Jan. 1977, pp. 63–66.

Demailly, P., et al., "Non–penetrating deep sclerectomy combined with a collagen implant in primary open–angle glaucoma. Medium–term retrospective results", J. Fr. Ophthalmol., vol. 19, No. 11, 1996, pp. 659–666. (Abstract only).

Fine, Ben S., et al., "A Clinicopathologic Study of Four Cases of Primary Open–Angle Glaucoma Compared to Normal Eyes", American Journal of Ophthalmology, vol. 91, No. 1, 1981, pp. 88–105.

Gharagozloo, N. Ziai, et al., "Unilateral exfoliation syndrome without glaucoma—a comparison of aqueous dynamica between affected and normal eyes", Glaucoma Paper Presentation, (abstract only —not dated).

Grierson, I., et al., "Age–related Changes in the Canal of Schlemm", Exp. Eye Res., (1984) 39, pp. 505–512.

Hamard, P., et al., "Deep nonpenetrating sclerectomy and open angle glaucoma. Intermediate results from the first operated patients", J. Fr. Ophthalmol., vol. 22 (j), Feb. 1999, pp. 25–31, (abstract only).

"Improving the flow: A survey of available implants", EW Practice Managment, Oct. 11, 1999, website "http://www.eyeworld.org/tooltime/999inserts.asp".

Johnson, M.C., et al, "The Role of Schlemm's Canal in Aqueous Outflow from the Human Eye", Investigative Ophthalmology & Visual Science, vol. 24, No. 3, Mar. 1983, pp. 320–325.

Karlen, M.E., et al., "Deep sclerectomy with collagen implant: Medium term results", Br. J. Ophthalmol. vol. 83, No. 1, Jan. 1999, pp. 6–11, (abstract only).

Mermoud, A., et al., "Comparison of deep sclerectomy with collagen implant and trabeculectomy in open–angle glaucoma", J. Cataract Refract. Surg., vol. 25, No. 3, Mar. 1999, pp. 323–331, (abstract only).

McMenamin, Paul G., et al., "Age–related Changes in the Human Outflow Apparatus", Ophthalmology, vol. 93, No. 2., Feb. 1986, pp. 194–209.

Moses, Robert A. et al., "Blood Reflux in Schlemm's Canal", Arch Ophthamol., vol. 97, Jul. 1979, pp. 1307–1310.

Moses, Robert A., "Circumferential Flow in Schlemm's Canal", American Journal of Ophthamology, vol. 88, No. 3, Part II, Sep. 1979, pp. 585–591.

Robinson, James C., et al., "Superior Cervical Ganglionectomy: Effects on Aqueous Human Flow in the Cynomolgus Monkey", Glaucoma Paper Presentation, (abstract only—not dated).

Samalonis, Lisa B., "New Horizons in the surgical treatment of glaucoma", EW Glaucoma, Oct. 11, 1999, website "http://www.eyeworld.org/sep99/999p62.asp".

Shields, M. Bruce, Textbook of Glaucoma, Fourth Ed., Williams & Wilkins Publihsers, 1998, pp. 5–31.

Spiegel, Detlev, et al., "Schlemm's Canal Implant: A New Method to Lower Intraocular Pressure in Patients with POAG", Ophthalmic Surgery and Lasers, vol. 30, No. 6, Jun. 1999, pp. 492–494.

Spiegel, D., "Surgical Glaucoma Therapy" in Benefits and Risks of Ophthalmological Therapy (Kampik & Grehn, Eds.) Ch. 7 (Germany 1998).

U.S. Clinical Wick Trials, Oct. 11, 1999, website http://www.cornea.org/us.htm. Allingham, R.R., et al., "Morphometric Analysis of Schlemm's Canal in Normal and Glaucomatous Human Eyes", Glaucoma Paper Presentation, (abstract only—not dated).

Welsh, N.H., et al., "The 'deroofing' of Schlemm's canal in patients with open–angle glaucoma through placement of a collagen drainage device", Ophthalmic Surg. Lasers, vol. 29, No. 3, Mar. 1998, pp. 216–226.

Wilson, Ellen D., "Implants offer choices for glaucoma surgeons", EW Glaucoma, Oct. 11, 1999, website "http://www.eyeorld.org/sep99/999p60.asp".

Jacobi, et al., "Microendoscopic trabecular surgery in glaucoma management", Ophthalmology, 1999, vol. 106, No. 3, pp. 538–544.

Johnstone, et al., "Cylindrical Tubular Structures Spanning From Trabecular Meshwork Across SC: Laboratory Studies With SEM, TEM & Tracers Correlated With Clinical Findings", American Glaucoma Society, $12^{th}$ Annual Meeting,, pp. 39.

Katz, L. Jay, "A call for innovative operatios for glaucoma", Arch Ophthalmology, Mar. 2000, vol. 118, pp. 412–413.

Luntz, et al., "Trabeculotomy ab externo and trabeculetomy in congenital and adult–onset glaucoma", American Journal of Ophthalmology, Feb. 1977, vol. 83, No. 2, pp. 174–179.

Matsumoto, et al., "Trabecular Meshwork Phagocytosis in Glaucomatous Eyes", Ophthalmologica 1997, vol. 211, pp. 147–152.

Nickells, Robert W., "Apoptosis of retinal ganglion cells in glaucoma: an update of the molecular pathways involved in cell death", Survey of Ophthalmology, vol. 43, Supplement 1, Jun. 1999, pp. S151–S161.

Putney, et al., "Intracellular C1 regulates Na–K–Cl cotransport activity in human trabecular meshwork cells", 1999 American Physiological Society, Sep. 1999, pp. C373–C383.

Radhakrishnan, et al., "Real–time optical coherence tomography of the anterior segment at 1310 nm", Arch Ophthalmology, Aug. 2001, vol. 119, pp. 1179–1185.

Rohen, Johannes W., "Anatomy of the aqueous outflow channels", Grune & Stratton, Harcourt Brace Jovanovich Publishers, Copyright 1986, edited by J.E. Carins, Glaucoma, vol. 1, Chapter 14, pp. 277–296.

Schwartz, et al., "Trabecular surgery" Arch Ophthalmol, vol. 92, Aug. 1974, pp. 134–138.

Shields, et al., "Aqueous humor dynamics", A Study Guide for Glaucoma, Williams & Wilkins, copyright 1982, pp. 6–43.

Strange, Kevin, "Cellular and molecular physiology of cell volume regulation", Library of Congress Cataloging in–Publication Data, CRC Press, Inc., Copyright 1993, pp. 311–321.

Tatton, W.G., "Apoptotic mechanisms in neurodegeneration: possible relevance to glaucoma", European Journal of Ophthalmology 1999, Jan.–Mar., vol. 9, Supplement 1, pp. S22–S29.

Tatton, et al., "Maintaining mitochondrial membrane impermeability: an opportunity for new therapy in glaucoma", Survey of Ophthalmology, vol. 45, Supplement 3, May 2001, pp. S277–S283.

Tripathi et al., "Functional Anatomy of the Anterior Chamber Angle", Biomedical Foundations of Ophthalmology, vol. 1, Chapter 10, pp. 1–74; Edited by Thomas Dune and Edward Jaeger, Revised Edition 1983, –Harper & Row, Publisher.

Hoerauf, et al., "Slit–lamp–adapted optical coherence tomography of the anterior segment", Graefe's Arch Clin. Exp. Ophthalmol., 2000, vol. 238: pp. 8–18.

Jacobi, et al., Goniocurettage for removing trabecular meshwork: Clinical Results of a New Surgical Technique in Advanced Chronic Open–Angle Glaucoma, American Journal of Ophthalmology, May 1999, pp. 505–510.

Jacobi, et al., "Bimanual trabecular aspiration in pseudoexfoliation glaucoma", Ophthalmology, 1998, vol. 105, No. 5, May 1998, pp. 886–894.

Grant, W.M., "Further studies on facility of flow through the trabecular meshwork", A.M.A. Archives of Ophthalmology, Oct. 1958, vol. 60, pp. 523–533.

Hill, et al., "Free–electron laser (FEL) Ablation of Ocular Tissues", Laser Med Sci 1998, vol. 13:219–226.

Hill, et al., "Laser trabecular ablation (LTA)", Laser in Surgery and Medicine, 1991, vol. 11, pp. 341–346.

* cited by examiner

SHUNT DEVICE AND METHOD FOR TREATING GLAUCOMA

CROSS-REFERENCE TO RELATED APPLICATIONS

This application is a continuation of U.S. patent application Ser. No. 10/242,385, filed Sep. 12, 2002, now U.S. Pat. No. 6,626,858, which is a continuation of U.S. patent Ser. No. 09/558,505, filed Apr. 26, 2000, now U.S. Pat. No. 6,450,984, which claims the benefit of U.S. Provisional Application No. 60/131,030, filed Apr. 26, 1999.

GOVERNMENT LICENSE

The U.S. Government has reserved a nonexclusive, irrevocable, royalty-free license in the invention with power to grant licenses for all governmental purposes.

TECHNICAL FIELD

The present invention is generally directed to a surgical treatment for glaucoma, and relates more particularly to a device and method for continuously decompressing elevated intraocular pressure in eyes affected by glaucoma by diverting aqueous humor from the anterior chamber of the eye into Schlemm's canal where post-operative patency can be maintained with an indwelling shunt which can be surgically placed to connect the canal with the anterior chamber.

BACKGROUND OF THE INVENTION

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's Canal is believed to be divided by septa into a series of autonomous, dead-end canals.

The aqueous fluid travels through the spaces between the trabecular beams, across the inner wall of Schlemm's canal into the canal, through a series of about 25 collecting channels that drain from Schlemm's canal and into the episcleral venous system. In a normal situation, aqueous production is equal to aqueous outflow and intraocular pressure remains fairly constant in the 15 to 21 mmHg range. In glaucoma, the resistance through the canalicular outflow system is abnormally high.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is not long lasting and fifty percent of patients develop an elevated pressure within five years. The laser surgery is not usually repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure enough, then filtering surgery is performed. With filtering surgery, a hole is made in the sclera and angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected half-thickness into the cornea. The anterior chamber is entered beneath the scleral flap and a section of deep sclera and trabecular meshwork is excised. The scleral flap is loosely sewn back into place. The conjunctival incision is tightly closed. Post-operatively, the aqueous fluid passes through the hole, beneath the scleral flap and collects in an elevated space beneath the conjunctiva. The fluid then is either absorbed through blood vessels in the conjunctiva or traverses across the conjunctiva into the tear film.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases.

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. The risk increases with the thin blebs that develop after MMC and 5-FU. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

When trabeculectomy doesn't successfully lower the eye pressure, the next surgical step often is an aqueous shunt device. An aqueous diversion device of the prior art is a silicone tube that is attached at one end to a plastic (polypropylene or other synthetic) plate. With an aqueous shunt device, an incision is made in the conjunctiva, exposing the sclera. The plastic plate is sewn to the surface of the eye posteriorly, usually over the equator. A full thickness hole is made into the eye at the limbus, usually with a needle. The tube is inserted into the eye through this hole. The external portion of the tube is covered with either donor sclera or pericardium. The conjunctiva is replaced and the incision is closed tightly.

With prior art aqueous diversion devices, aqueous drains out of the eye through the silicone tube to the surface of the eye. Deeper orbital tissues then absorb the fluid. The outside end of the tube is protected from fibroblasts and scarring by the plastic plate. Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. Many physicians tie an absorbable suture around the tube and wait for the suture to dissolve post-operatively at which time enough scar tissue has hopefully formed around the plate. Some devices contain a pressure-sensitive valve within the tube, although these valves may not function properly. The surgery involves operating in the posterior orbit and many patients develop an eye muscle imbalance and double vision post-operatively. With prior art aqueous shunt devices, a pathway is created for bacteria to get into the eye and endophthalmitis can potentially occur.

The prior art includes a number of such aqueous shunt devices, such as U.S. Pat. No. 4,936,825 (providing a tubular shunt from the anterior chamber to the corneal surface for the treatment of glaucoma), U.S. Pat. No. 5,127,901 (directed to a transscleral shunt from the anterior chamber to the subconjunctival space), U.S. Pat. No. 5,180,362 (teaching a helical steel implant that is placed to provide drainage from the anterior chamber to the subconjunctival space), and U.S. Pat. No. 5,433,701 (generally teaching shunting from the anterior chamber to the scleral or conjunctival spaces).

In addition to the prior art aqueous shunt devices described above, other prior art devices for glaucoma surgery have used setons, or other porous, wick-like components to divert and convey excess aqueous from the anterior chamber to the exterior ocular surface. Examples include U.S. Pat. Nos. 4,634,418 and 4,787,885 (teaching the surgical treatment of glaucoma using an implant that consists of a triangular seton (wick)), and U.S. Pat. No. 4,946,436, (teaching the use of a porous device to shunt anterior chamber to subscleral space). These patents do not teach placement in Schlemm's canal.

Some prior art references for glaucoma management have been directed at Schlemm's canal, but these have not involved the placement of long-term, indwelling shunts. U.S. Pat. No. 5,360,399 teaches the temporary placement of a plastic or steel tube with preformed curvature in Schlemm's canal with injection of a viscous material through the tube to hydraulically expand and hydrodissect the trabecular meshwork. The tube is removed from the canal following injection. Because the tube is directed outwardly from the eye for injection access, the intersection of the outflow element with the preformed curved element within Schlemm's canal is at about a 90 degree angle relative to the plane of the curvature, and 180 degrees away from the anterior chamber. Therefore, at no time does any portion of the '399 device communicate with the anterior chamber. Furthermore, relative to that portion within Schlemm's canal, this tube has a larger diameter injection cuff element, which serves as an adapter for irrigation. Therefore, this device is not adapted for shunting aqueous between the anterior chamber and Schlemm's canal.

Most of the problems that have developed with current glaucoma treatment devices and procedures have occurred because aqueous fluid is drained from inside of the eye to the surface of the eye. A need exists, then, for a more physiologic system to enhance the drainage of aqueous fluid from the anterior chamber into Schlemm's canal. In the vast majority of glaucoma patients, the resistance problem lies between Schlemm's canal and the anterior chamber. The canal itself, the collecting channels and the episcleral venous system all are intact. Enhancing aqueous flow directly into Schlemm's canal would minimize the scarring that usually occurs with external filtration procedure since the internal angle region is populated with a single line of nonproliferating trabecular cells. Enhancing aqueous flow directly into Schlemm's canal would minimize hypotony since the canal is part of the normal outflow system and is biologically engineered to handle the normal volume of aqueous humor. Enhancing aqueous flow directly into Schlemm's canal would eliminate complications such as endophthalmitis and leaks.

SUMMARY OF THE INVENTION

The present invention is directed to a novel shunt and an associated surgical method for the treatment of glaucoma in which the shunt is placed to divert aqueous humor from the anterior chamber of the eye into Schlemm's canal. The present invention therefore facilitates the normal physiologic pathway for drainage of aqueous humor from the anterior chamber, rather than shunting to the sclera or another anatomic site as is done in most prior art shunt devices. The present invention is further directed to providing a permanent, indwelling shunt to provide increased egress of aqueous humor from the anterior chamber to Schlemm's canal for glaucoma management.

DETAILED DESCRIPTION OF PRESENT INVENTION

The present invention provides an aqueous humor shunt device to divert aqueous humor in the eye from the anterior chamber into Schlemm's canal, in which the shunt device comprises a distal portion having at least one terminal aspect sized and shaped to be circumferentially received within a portion of Schlemm's canal, and a proximal portion having at least one terminal aspect sized and shaped to be received within the anterior chamber of the eye, wherein the device permits fluid communication between the proximal portion in the anterior chamber to the distal portion in Schlemm's canal. Fluid communication can be facilitated by an aqueous humor directing channel in either the proximal or distal portions, as described below. Fluid communication can also be facilitated by a wicking function of a solid proximal or distal portions of the device, for example.

The present invention also provides embodiments of an inventive shunt comprising a body of biocompatible material of a size and shape adapted to be at least partially circumferentially received within a portion of Schlemm's canal to divert aqueous humor from the anterior chamber of the human eye to and within Schlemm's canal, and wherein the body facilitates the passage of aqueous humor from the anterior chamber into Schlemm's canal. This embodiment of the device of the present invention can be produced without the proximal portion of the previous embodiment extending into the anterior chamber. An aqueous humor directing channel can facilitate the passage of aqueous humor from the anterior chamber into Schlemm's canal. Fluid communication can also be facilitated by a wicking function of a solid body portion, for example.

The invention contemplates many different configurations for an aqueous humor directing channel, provided that each assists in channeling aqueous humor from the anterior chamber to Schlemm's canal, such as by providing a lumen, trough, wick or capillary action. For example, the aqueous humor directing channel can be a fully enclosed lumen, a partially enclosed lumen, or a trough-like channel that is at least partially open. The invention contemplates that a solid monofilament or braided polymer, such as proline, can be inserted into Schlemm's canal to provide a wicking function to facilitate the passage of aqueous humor from the anterior chamber to Schlemm's canal. Such a wicking extension can also be grooved or fluted along any portion of the length thereof, so as to be multi-angular or star-shaped in cross-section. The devices of the present invention can be constructed of a solid, matrix, mesh, fenestrated, or porous material, or combinations thereof.

Traditional glaucoma teaching states that Schlemm's canal in an adult is divided by septa into separate canals, rendering the complete passage of a suture impossible. Preliminary studies on adult human eye bank eyes have shown that Schlemm's canal is, indeed, patent. A suture can be passed through the entire circumference of the canal. It has not been heretofore determined that Schlemm's canal is patent throughout its circumference in normal adult individuals, as opposed to being divided by septae into multiple dead end canals. The invention utilizes this knowledge to access Schlemm's canal and to create and maintain the natural physiologic egress of aqueous humor from the anterior chamber to Schlemm's canal and to the collecting channels.

The present invention also provides methods of use of the shunt devices. One embodiment of the present invention is directed to a surgical method to divert aqueous humor from the anterior chamber of the eye into Schlemm's canal with a device that is implanted to extend from within the anterior chamber to Schlemm's canal. The portion of the device extending into Schlemm's canal can be fashioned from a flexible material capable of being received within a portion of the radius, curvature, and diameter of Schlemm's canal. All or parts of the device may be solid, porous, tubular, trough-like, fenestrated, or pre-curved.

Figure 1A:
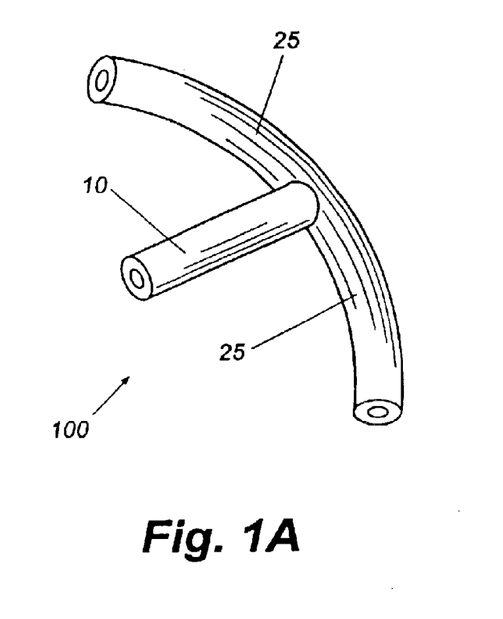
FIG. 1A is an illustration showing an overhead perspective view of one embodiment of the present invention, in which the inventive shunt is comprised of tubular elements extending bi-directionally within Schlemm's canal.
Figure 1B:
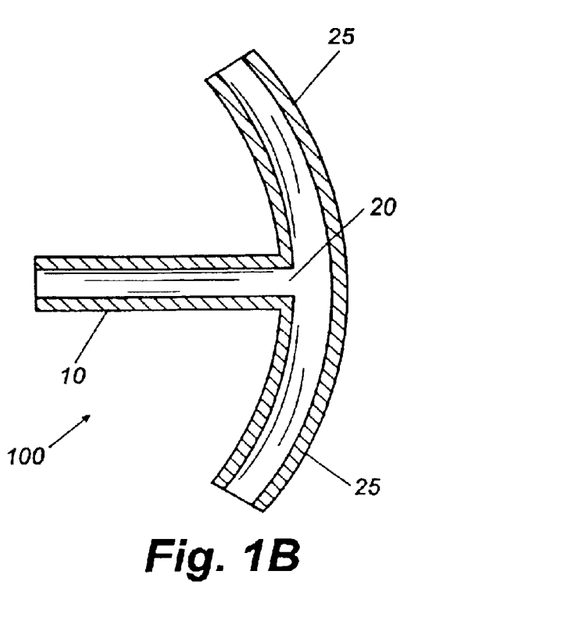
FIG. 1B is an overhead view of the embodiment of the present invention shown in FIG. 1A, with phantom lines detailing the internal communication between the lumens of the tubular elements comprising the inventive device.

One embodiment of the present invention is illustrated in FIG. 1A, in which the shunt device 100 is shown in a side view. The shunt device 100 of this embodiment is comprised of two portions, a proximal portion 10 which joins a distal portion 25. The proximal portion 10 and distal portion 25 shown create an enclosed tubular channeling structure. The total length of the distal portion 25 may be between about 1 and 40 mm, preferably about 6 mm. The same embodiment of the present invention is illustrated with phantom lines showing the internal fluid communication path in FIG. 1B. The lumen or channeling space defined by the walls of the proximal portion 10 and the distal portion(s) 25 are continuous at their junction at the distal portion portal 20.

Figure 1C:
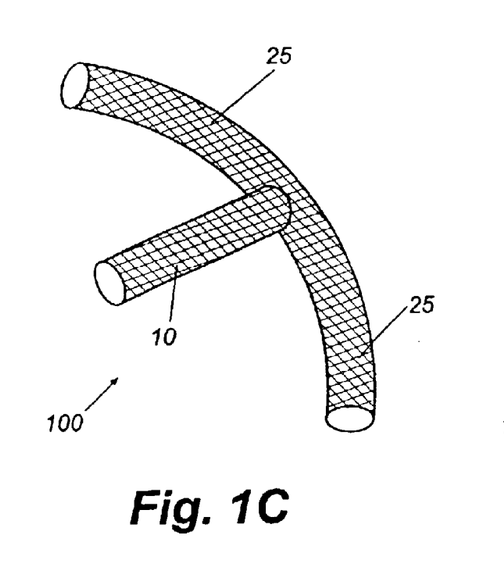
FIG. 1C is an illustration showing an overhead perspective view of one embodiment of the present invention, in which the inventive shunt is comprised of mesh tubular elements extending bi-directionally within Schlemm's canal.
Figure 1D:
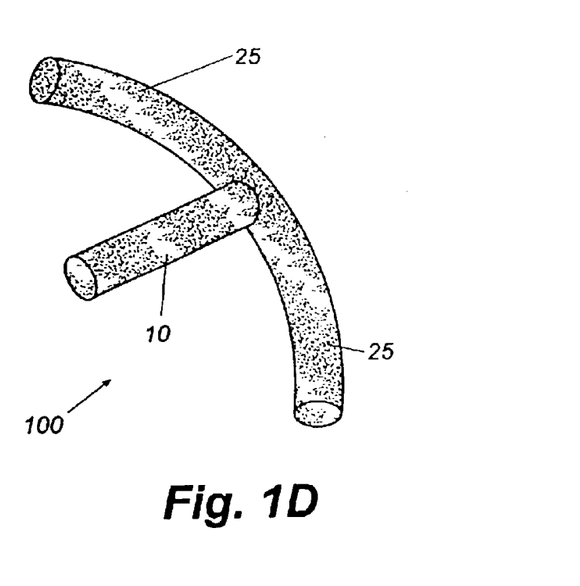
FIG. 1D is an illustration showing an overhead perspective view of one embodiment of the present invention, in which the inventive shunt is comprised of solid, porous elements extending bi-directionally within Schlemm's canal.

An alternate embodiment of the present invention is shown in FIG. 1C, in which the shunt device 100 is comprised of two luminal mesh elements, with a proximal portion 10 which joins a distal portion 25. Yet another embodiment of the present invention is shown in FIG. 1D, in which the shunt device 100 is comprised of two solid, porous elements which may provide wick-like fluid communication therethrough, with a proximal portion 10 which joins a distal portion 25.

Figure 1E:
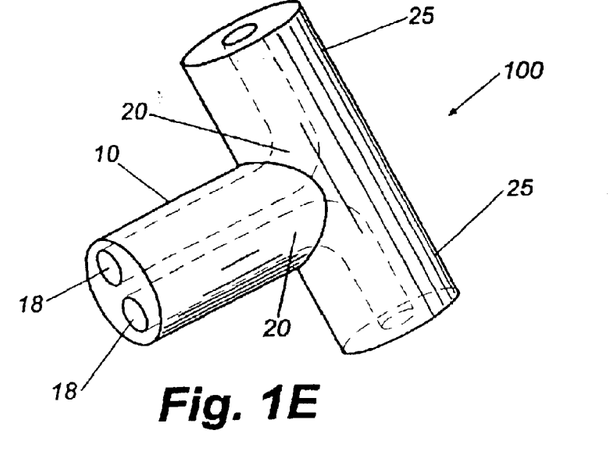
FIG. 1E is an overhead perspective view of another embodiment of the present invention, with phantom lines detailing the internal communication between the two proximal lumens and the single distal lumen of the inventive device.

An alternate embodiment of the present invention is shown in FIG. 1E, in which the shunt device 100 is comprised of a proximal portion 10 having two lumens therein terminating in proximal portion portals 18. The distal portion 25 shaped and sized to be received within Schlemm's canal extends in either direction having separate lumens traversing therethrough from each of the distal portion portals 20.

Figure 2:
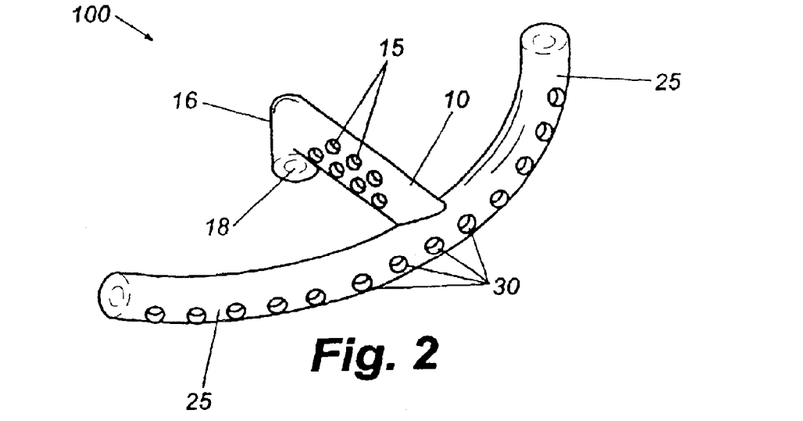
FIG. 2 is an illustration showing another embodiment of the present invention, in which the inventive shunt is comprised of perforated tubular elements and with an angulated terminal aspect of the proximal portion.

Other examples of embodiments of the present invention are shown in FIGS. 2–5D. FIG. 2 shows an embodiment of the inventive shunt in which the device 100 is tubular and fenestrated (15, 30) in its configuration, with an acute (<90) angle of junction between the proximal portion 10 and the plane defined by the distal portion 25. Such fenestrations (15, 30) may be placed along any portion of the device 100 to facilitate the passage of fluid therethrough, but are particularly directed towards the collecting channels of the eye. FIG. 2 further shows an alternate embodiment of the present invention in which the terminal aspect 16 of the proximal portion is angulated toward the iris 40 with respect to the main axis of the proximal portion 10, with the portal 18 of the proximal portion directed toward the iris 40. In alternate embodiments as shown in FIG. 6C, the portal 18 of the proximal portion 16 is directed away from the iris 40.

Figure 3A:
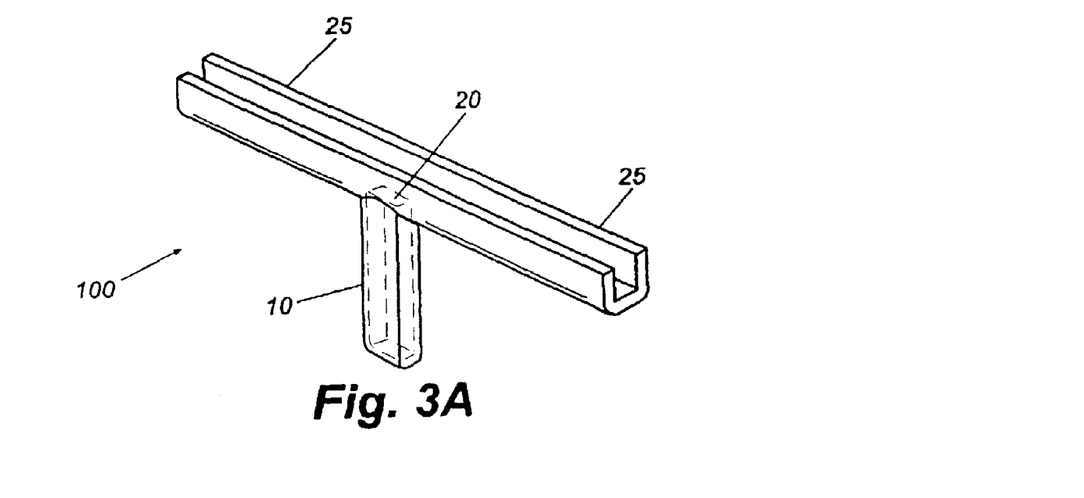
FIG. 3A is an illustration showing a perspective of another embodiment of the present invention in which the inventive shunt is comprised of elements that are partially tubular and partially open in their configuration.

FIG. 3A shows an embodiment of the inventive shunt in which a portion of the channeling device is enclosed and tubular in configuration at the junction of the proximal portion 10 and the distal portion 25, but where the distal portion 10 is a trough-like channel. The distal portion portal 20 is also shown. The invention contemplates that any portion of the device 100 can be semi-tubular, open and trough-like, or a wick-like extension. Tubular channels can be round, ovoid, or any other enclosed geometry. Preferably the non-tubular trough-like aspects are oriented posteriorly on the outer wall of the canal to facilitate aqueous humor drainage to the collecting channels of the eye, as shown in FIG. 3A.

Figure 3B:
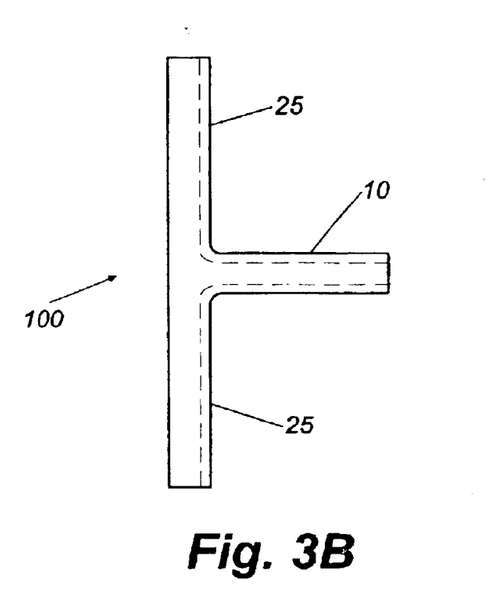
FIG. 3B is an illustration showing a top view of the embodiment of the present invention in FIG. 3A, with phantom lines detailing the internal communication of the device.
Figure 3C:
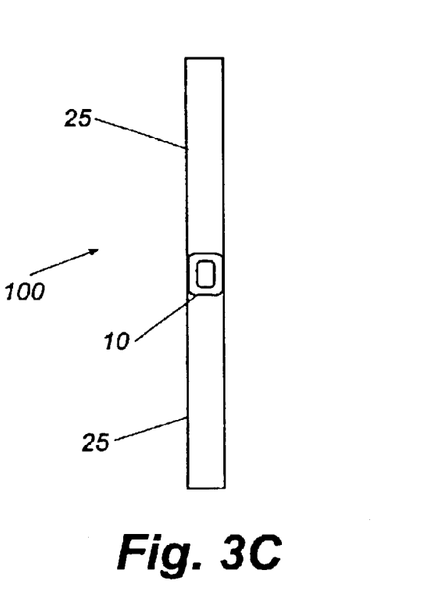
FIG. 3C is an illustration showing a side view from the proximal end of the embodiment of the present invention in FIG. 3A.

FIG. 3B shows an overhead view of the embodiment of the inventive shunt of FIG. 3A, further detailing the relationship among the proximal portion 10 and the distal portion 25. The aqueous humor directing channel is shown in dashed lines. FIG. 3C shows a proximal view of the embodiment of the inventive shunt of FIG. 3A, further detailing the relationship among the proximal portion 10 and the distal portion 25.

Figure 3D:
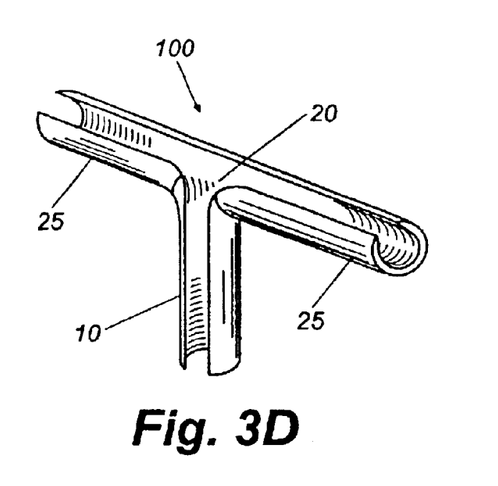
FIG. 3D is an illustration showing a perspective of another embodiment of the present invention in which the inventive shunt is comprised of elements that are partially open and trough-like in their configuration.

FIG. 3D shows another embodiment of the inventive shunt in which the structure of the device 100 comprises an aqueous humor directing channel that is both open and curved in a continuous trough-like configuration along the proximal portion 10 and the distal portion 25. The distal portion portal 20 is also an open trough-like channel.

Figure 4:
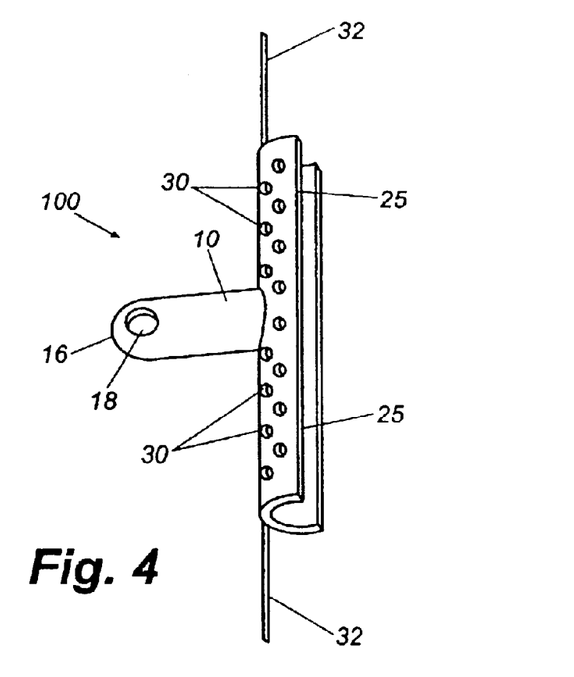
FIG. 4 is an illustration showing another embodiment of the present invention, in which the inventive shunt is comprised of distal elements having wicking extensions at their terminal ends, and in which the proximal portion has a sealed, blunted tip with a portal continuous with the lumen of the proximal portion, oriented to face away from the iris when the device is implanted in Schlemm's canal.

FIG. 4 shows another embodiment of the inventive shunt with the addition of aqueous humor-wicking extensions 32 which are either continuous with, or attached to the terminal aspects of the distal portion 25. The wicking extensions 32 can be fashioned from a monofilament or braided polymer, such as proline, and preferably have a length of 1.0 mm to 16.0 mm. Furthermore, the proximal portion 10 is curved with a sealed, blunted tip 16 and contains a portal 18 in fluid communication with the lumen of the proximal portion and oriented to face away from the iris when the shunt device 100 is implanted in its intended anatomic position. The shunt device 100 can also help to maintain the patency of Schlemm's canal in a stenting fashion.

Figure 5A:
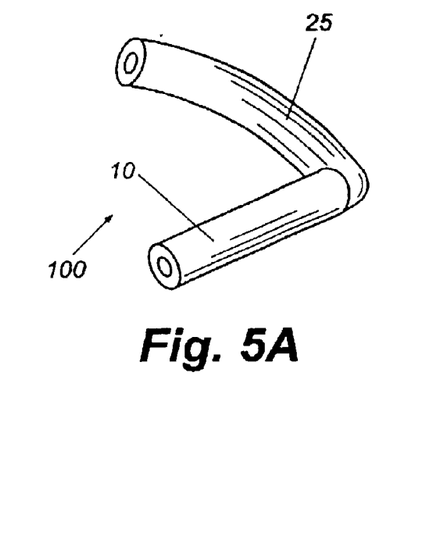
FIG. 5A is an illustration showing another embodiment of the inventive shunt in which a portion of the device enters Schlemm's canal in only one direction and shunts fluid in a non-linear path from the anterior chamber.

FIG. 5A shows another embodiment of the inventive shunt in which the proximal portion 10 joins a single, curved distal portion 25 in a "V-shaped," tubular configuration. The embodiment shown in FIG. 5A can also have a portal (not shown) in the distal portion 25 adjacent to the junction with the proximal portion 10 in order to facilitate bi-directional flow of fluid within the canal. Fenestrations and non-tubular, trough-like terminal openings are contemplated in all embodiments of the invention, and these fenestrations and openings may be round, ovoid, or other shapes as needed for optimum aqueous humor channeling function within the anatomic spaces involved.

Figure 5B:
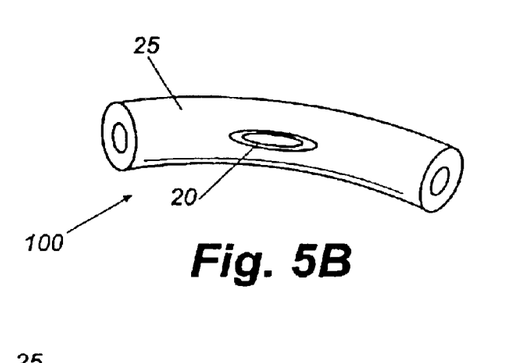
FIG. 5B is an illustration showing an alternative embodiment of the inventive shunt in which the entire shunt is placed within Schlemm's canal but contains a fenestration to maintain fluid egress of aqueous humor from the anterior chamber to Schlemm's canal.

FIG. 5B shows another embodiment of the inventive shunt in which the body or device 100 comprises only a single, curved distal portion 25 which contains a distal portion portal 20 oriented towards the anterior chamber to allow egress of aqueous humor from the anterior chamber to Schlemm's canal. The body of this device can have a length of about 1.0 mm to 40 mm, preferably about 6 mm. The external diameter can be about 0.1 mm to 0.5 mm, or about 0.3 mm.

Figure 5C:
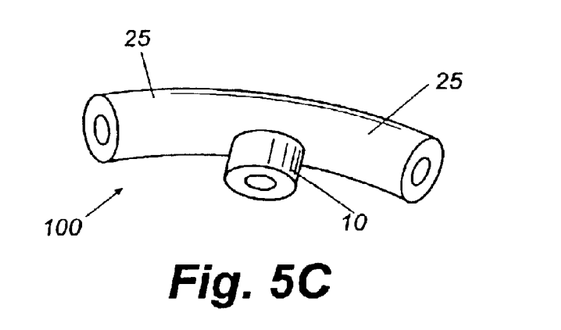
FIG. 5C is an illustration showing a side view of one embodiment of the present invention, in which the inventive shunt is comprised of tubular elements, with a proximal portion extending towards the anterior chamber that is shorter relative to the distal portions which extend bi-directionally within Schlemm's canal.

FIG. 5C shows another embodiment of the inventive shunt in which the device 100 comprises a bi-directional tubular distal portion 25 which is intersected by a proximal portion 10 which is short in length relative to the distal portion 25 and is directed towards the anterior chamber.

Figure 5D:
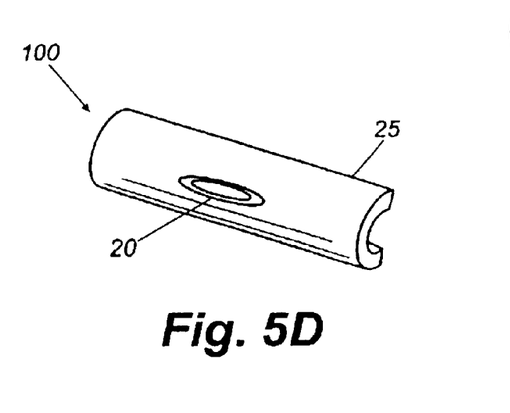
FIG. 5D is an illustration showing an alternative embodiment of the inventive shunt comprised of a partially open trough-like element which is placed within Schlemm's canal but contains a portal to maintain fluid egress of aqueous humor from the anterior chamber to Schlemm's canal.

FIG. 5D shows still another embodiment of the inventive shunt in which the device 100 comprises a bi-directional, trough-like, curved distal portion 25 for insertion into Schlemm's canal, which contains a distal portion portal 20 oriented to allow egress of aqueous humor from the anterior chamber, wherein the trough-like distal portion 25 is oriented to open toward the collecting channels to facilitate the egress of aqueous humor.

Figure 5E:
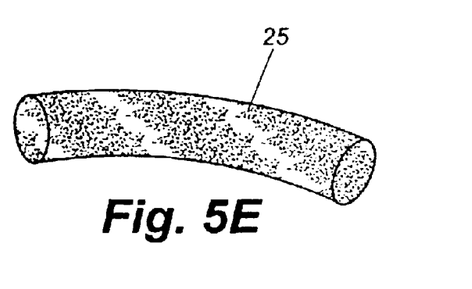
FIG. 5E is an illustration showing an alternative embodiment of the inventive shunt comprised of a solid, but porous wick-like element which is placed within Schlemm's canal

FIG. 5E shows another embodiment of the inventive shunt in which the device 100 comprises a bi-directional, solid distal portion 25 for insertion into Schlemm's canal to facilitate the egress of aqueous humor from the canal to the collecting channels in a wicking capacity. The solid distal portion 25 can be porous or non-porous.

As the inventive device is an implant, it can be fabricated from a material that will be compatible with the tissues and fluids with which it is in contact. It is preferable that the device not be absorbed, corroded, or otherwise structurally compromised during its in situ tenure. Moreover, it is equally important that the eye tissues and the aqueous remain non-detrimentally affected by the presence of the implanted device. A number of materials are available to meet the engineering and medical specifications for the shunts. In the exemplary embodiments of the present invention, the shunt device 100 is constructed of a biologically inert, flexible material such as silicone or similar polymers. Alternate materials might include, but are not limited to, thin-walled Teflon, polypropylene, other polymers or plastics, metals, or some combination of these materials. The shunt device 100 may be constructed as either porous or solid in alternate embodiments. The material can contain a therapeutic agent deliverable to the adjacent tissues.

In the embodiments shown in FIGS. 1–4, the proximal portion 10 joins the distal portion(s) 25 at an angle sufficient to allow the placement of the proximal portion 15 within the anterior chamber of the eye when the distal portion 25 is oriented in the plane of Schlemm's canal. The proximal portion 10 is preferably of sufficient length, about 0.1 to 3.0 mm or about 2.0 mm, to extend from its junction with the distal portion 25 in Schlemm's canal towards the adjacent space of the anterior chamber. While many geometries can be used for channeling aqueous humor, the diameter or width of the proximal portion 10 can be sized to yield an internal diameter of between about 0.1 and 0.5 mm, preferably 0.20 mm, for a tubular or curved shunt, or a comparable maximal width for a shunt with a multiangular configuration. In other embodiments, the proximal portion is a non-luminal, non-trough-like wicking extension that provides an aqueous humor directing channel along the length thereof.

Because the nature of the iris 40 is such that it tends to comprise a plurality of rather flaccid fimbriae of tissue, it is desirable to avoid said fimbriae from being drawn into the lumen of an implant, thus occluding the shunt device. Therefore, the proximal portion 10 may contain a plurality of fenestrations to allow fluid ingress, arranged to prevent occlusion by the adjacent iris. Alternately, the proximal portion 10 may comprise only a proximal portion portal 18 in the form of a fenestration oriented anteriorly to provide continuous fluid egress between the anterior chamber of the eye and the directing channel of the shunt. Said fenestrations may be any functional size, and circular or noncircular in various embodiments of the present invention. In addition, a porous structural material can assist in channeling aqueous humor, while minimizing the potential for intake of fimbriae.

Furthermore, the proximal portion 10 may be positioned sufficiently remote from the iris 40 to prevent interference therewith, such as by traversing a more anterior aspect of the trabecular meshwork into the peripheral corneal tissue. In yet another possible embodiment, as shown in FIG. 6C, the device 100 may comprise a proximal portion 10 in which the terminal aspect of said proximal portion 10 is curved or angled toward the iris 40, and with a blunted, sealed tip 16 and a portal 18 oriented anteriorly to face away from the underlying iris 40. Such a configuration would tend to decrease the possibility of occlusion of the shunt device by the iris 40.

The device 100 may contain one or more unidirectional valves to prevent backflow into the anterior chamber from Schlemm's canal. The internal lumen for an enclosed portion of the device or the internal channel defined by the edges of an open portion of the device communicates directly with the inner lumen or channel of the distal portion at the proximal portion portal 20.

The distal portion 25 may have a pre-formed curve to approximate the 6.0 mm radius of Schlemm's canal in a human eye. Such a pre-formed curvature is not required when flexible material is used to construct the shunt device 100. The distal portion 25 may be of sufficient length to extend from the junction with the proximal portion 10 through any length of the entire circumference of Schlemm's canal. Embodiments having a distal portion 25 that extends in either direction within Schlemm's canal can extend in each direction about 1.0 mm to 20 mm, or about 3.0 mm, to permit circumferential placement through Schlemm's canal. The diameter of width of the distal portion 25 can be sized to yield an outer diameter of between about 0.1 and 0.5 mm, or about 0.3 mm, for a tubular or curved shunt, or a comparable maximal width for a shunt with a multiangular configuration. The distal portion 25 may contain a plurality of fenestrations to allow fluid egress, arranged to prevent occlusion by the adjacent walls of Schlemm's canal. In other embodiments, the distal portion is a non-luminal, non-trough-like wicking extension that provides an aqueous humor directing channel along the length thereof.

In the exemplary embodiments of the present invention, the shunt device may be either bi-directional, with the distal portion of the implant intersecting with the proximal portion in a "T-shaped" junction as shown in FIGS. 1A–1E, 2, 3A–3D, 4 and 5C, or uni-directional, with a "V-shaped" junction of the proximal and distal shunt portions, as shown in FIG. 5A. A bi-directional shunt device can have a distal portion that is threaded into opposing directions within Schlemm's canal. In the case of the uni-directional shunt, only the distal shunt portion is placed within Schlemm's canal. In these exemplary embodiments, "non-linear fluid communication" means that at least some portion of the shunt through which fluid passes is not in a straight line. Examples of non-linear shunts are the above described bi-directional "T" shapes, and the uni-directional "V" shapes, or shunts having two channel openings which are not in straight alignment with each other.

Figure 6A:
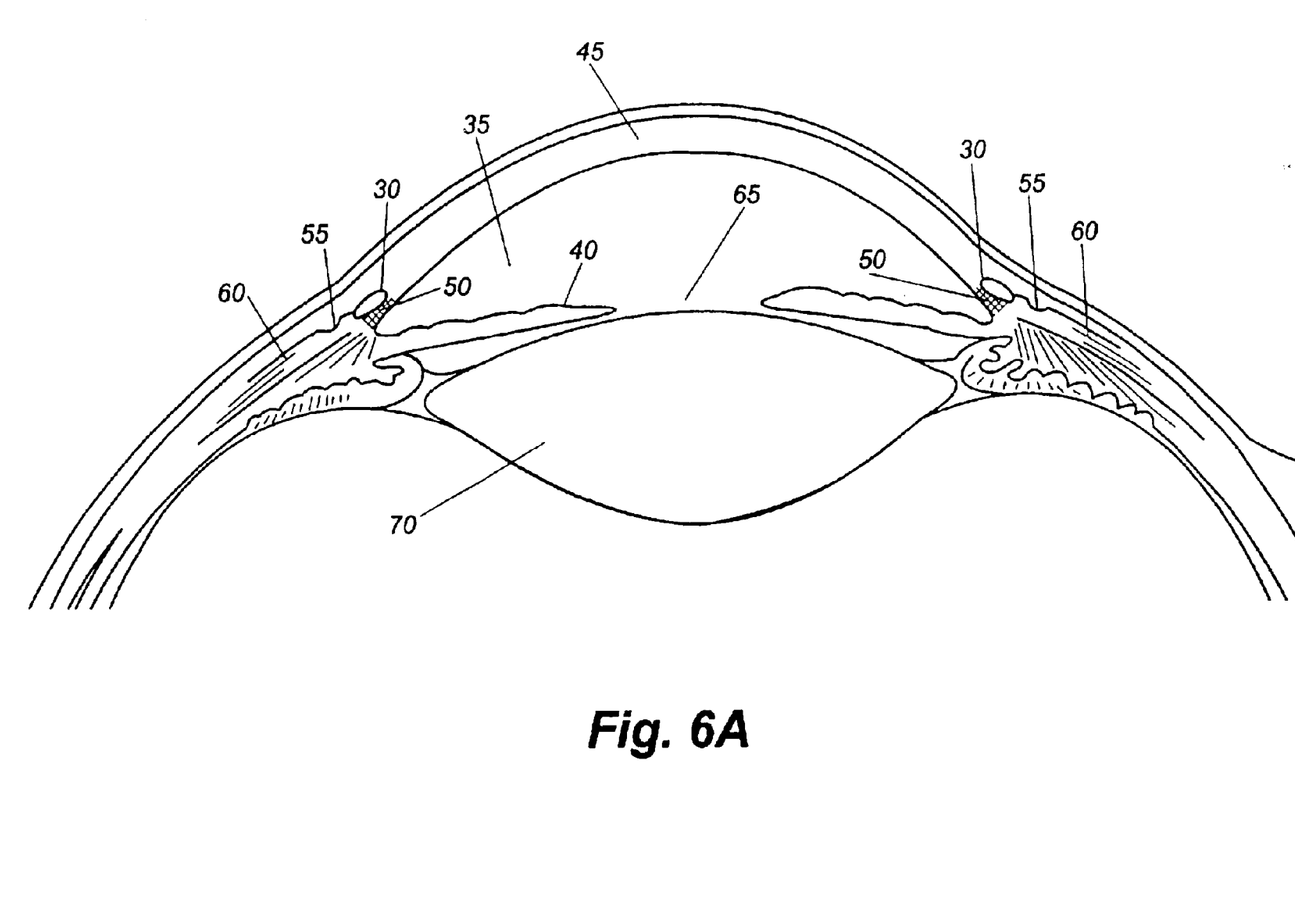
FIG. 6A is an illustration showing certain anatomic details of the human eye.
Figure 6B:
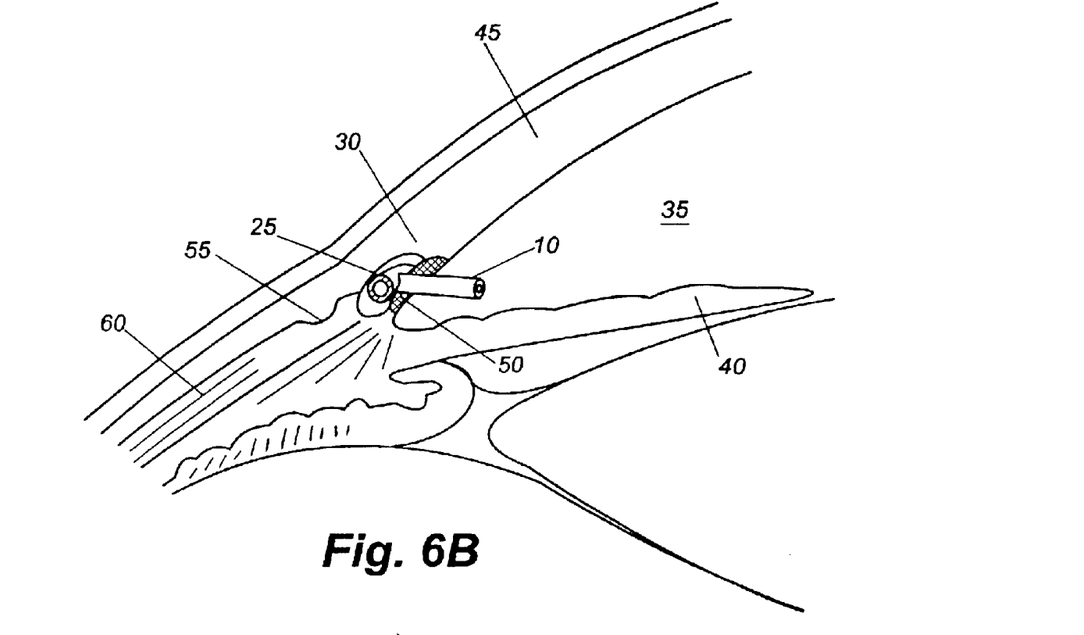
FIG. 6B is a cross-sectional illustration showing the anatomic relationships of the surgical placement of an exemplary embodiment of the present invention.
Figure 6C:
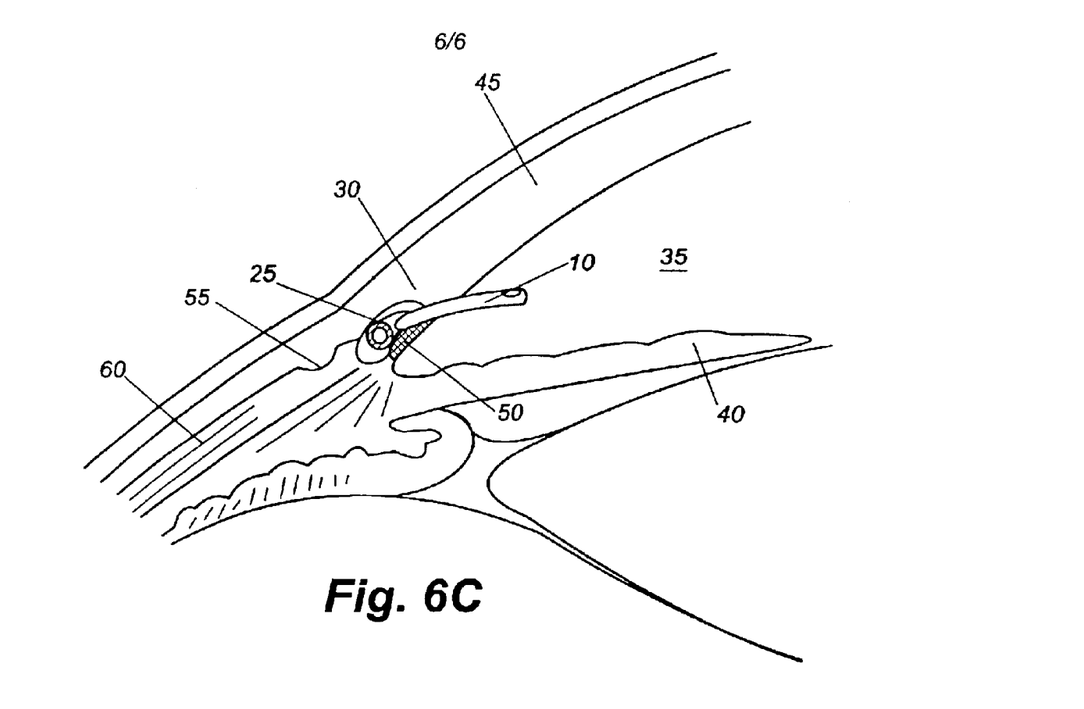
FIG. 6C is a cross-sectional illustration showing the anatomic relationships of the surgical placement of another exemplary embodiment of the present invention in which the proximal portion has an angulated terminal aspect with a sealed, blunted tip with a portal continuous with the lumen of the proximal portion, oriented to face away from the iris when the device is implanted in Schlemm's canal.

The surgical anatomy relevant to the present invention is illustrated in FIG. 6A. Generally, FIG. 6A shows the anterior chamber 35, Schlemm's canal 30, the iris 40, cornea 45, trabecular meshwork 50, collecting channels 55, episcleral veins 60, pupil 65, and lens 70. FIG. 6B illustrates the surgical placement of the exemplary embodiment of the present invention, with the relevant anatomic relationships. It should be noted that the inventive device is designed so that placement of the distal portion 25 within Schlemm's canal 30 results in an orientation of the proximal portion 10 within the anterior chamber 35 within the angle defined by the iris 40 and the inner surface of the cornea 45. Therefore, if the plane defined by Schlemm's canal is defined as zero degrees, the proximal portion 10 can extend therefrom at an angle of between about +60 degrees towards the cornea 45 or −30 degrees toward the iris 40, more preferably in the range of 0 to +45 degrees. This range may vary in individuals having a slightly different location of Schlemm's canal 30 relative to the limbal angle of the anterior chamber 35.

In yet another embodiment of the present invention not shown, the shunt device 100 is configured with one distal portion 25 which is tubular to provide a shunting functionality and a plurality of proximal portions 10 which provide an anchoring function to stabilize the overall implant device, in addition to providing fluid communication from the anterior chamber to Schlemm's Canal.

The surgical procedure necessary to insert the device requires an approach through a conjunctival flap. A partial thickness scleral flap is then created and dissected half-thickness into clear cornea. The posterior aspect of Schlemm's canal is identified and the canal is entered posteriorly. The anterior chamber may be deepened with injection of a viscoelastic and a miotic agent. The proximal portion of the shunt is then inserted through the inner wall of Schlemm's canal and trabecular meshwork into the anterior chamber within the angle between the iris and the cornea. In some cases, as incision may be needed from Schlemm's canal through the trabecular meshwork into the anterior chamber to facilitate passage of the proximal portion therethrough. One arm of the distal portion of the shunt device is grasped and threaded into Schlemm's canal. In a similar fashion, the other arm of the distal portion of the shunt device (when present) is inserted into Schlemm's canal in the opposing direction from the first. The scleral flap and conjunctival wound are closed in a conventional manner.

While the above-described embodiments are exemplary, the invention contemplates a wide variety of shapes and configurations of the shunt to provide fluid communication between the anterior chamber and Schlemm's canal. The above-described embodiments are therefore not intended to be limiting to the scope of the claims and equivalents thereof.

What is claimed is:

1. An ocular device comprising:
   a solid-walled tubular body for implantation into Schlemm's canal of a living eye comprising a portion for insertion into said canal, and a portion sized to extend from a position within said canal to a position within an anterior chamber of said eye; and
   wherein said tubular body comprises a metal and is configured and dimensioned such that implantation of said tubular body in living tissue of said canal permits dynamic flow of aqueous humor toward an episcleral venous system of said eye.

2. The ocular device of claim 1, wherein said tubular body comprises a proximal end with an opening, said proximal end being oriented between 0° and 90° with respect to a line extending between respective ends of said canal.

3. The ocular device of claim 1, wherein said tubular body comprises a proximal end with an opening, said proximal end being oriented between 0° and 45° with respect to a line extending between respective ends of said canal.

4. The ocular device of claim 1, wherein said tubular body comprises open ends and is configured and dimensioned to permit communication between said open ends of substantially all aqueous humor entering said tubular body.

5. The ocular device of claim 1, wherein said tubular body defines an aqueous humor directing channel extending between ends of said tubular body that is sized to permit flow of aqueous humor therein.

6. The ocular device of claim 5, wherein said aqueous humor directing channel in said tubular body is sized to wick aqueous humor therein.

7. The ocular device of claim 1, wherein said tubular body further comprises a therapeutic agent.

8. The ocular device of claim 1, wherein said flexible portion of said tubular body is adapted to conform to a radius of curvature of 6 mm.

9. The ocular device of claim 1, wherein said tubular body comprises first and second integrally formed sections disposed transverse to each other.

10. The ocular device of claim 1, wherein said tubular body is configured and dimensioned to permit dynamic flow of aqueous humor at a flow rate below about 2.5 microliters per minute.

11. The ocular device of claim 1, wherein said tubular body is configured and dimensioned to permit dynamic flow of aqueous humor at a flow rate sufficient to maintain eye pressure above 6.0 mmHg.

12. The ocular device of claim 1, wherein said tubular body is configured and dimensioned to permit dynamic flow of aqueous humor at a flow rate that maintains eye pressure between 15 mmHg and 21 mmHg.

13. The ocular device of claim 1, wherein said tubular body has an inner diameter of between 0.1 mm and 0.5 mm.

14. The ocular device of claim 1, wherein said tubular body defines an aqueous humor directing channel with a maximum width between 0.2 mm and 0.5 mm.

15. The ocular device of claim 1, wherein said tubular body further comprises an anchor portion for stabilizing the tubular body in Schlemm's canal.

16. The ocular device of claim 1, wherein said tubular body comprises an arcuate outer surface.

17. The ocular device of claim 1, wherein said tubular body comprises a cylindrical outer cross-section.

18. The ocular device of claim 1, wherein said tubular body is curved.

19. An ocular device comprising:
a solid-walled tubular body for implantation into Schlemm's canal of a living eye wherein at least a portion of the tubular device comprises a non-linear aqueous humor directing channel; and
wherein said tubular body is configured and dimensioned such that implantation of said tubular body in living tissue of said canal directs dynamic flow of aqueous humor from an anterior chamber of said living eye and through said non-linear aqueous humor directing channel toward episcleral veins.

20. The device of claim 19, wherein a portion of the device inserts into the anterior chamber of the eye.

21. The device of claim 19, wherein the device comprises a metal.

22. The device of claim 19, wherein at least a portion of said tubular body comprises a rigid portion.

23. The device of claim 19, wherein the device comprises a therapeutic agent.

24. The device of claim 19, wherein the device comprises a T-shape.

25. The device of claim 24, wherein one portion of the T-shaped device inserts into the anterior chamber of the eye, and two portions of the device insert within Schlemm's canal in a substantially bi-directional manner.

26. The device of claim 19, wherein the device comprises a V-shape.

27. The ocular device of claim 26, wherein at least a portion of said tubular body is shaped as an open trough.

28. The ocular device of claim 26, wherein said tubular body comprises first and second elongate lumens.

29. The ocular device of claim 28, wherein a portion of the first elongate lumen is parallel to a portion of the second elongate lumen.

30. The ocular device of claim 29, wherein the first and second elongate lumens are separated from each other.

31. The ocular device of claim 28, wherein a portion of the first elongate lumen is disposed transverse to a portion of the second elongate lumen.

32. An ocular device comprising:
a solid-walled tubular body adapted to be received in Schlemm's canal of a living eye;
wherein the tubular body is dimensioned to allow non-linear fluid communication; and
wherein said tubular body is configured and dimensioned such that implantation of said tubular body in living tissue of said canal directs dynamic flow of aqueous humor toward episcleral veins.

33. The device of claim 32, wherein a portion of the device inserts into the anterior chamber of the eye.

34. The device of claim 32, wherein the device comprises a metal.

35. The device of claim 32, wherein the device comprises a therapeutic agent.

36. The device of claim 32, wherein the device comprises a T-shape.

37. The device of claim 36, wherein one portion of the T-shaped device inserts into the anterior chamber of the eye, and two portions of the device insert within Schlemm's canal in a substantially bi-directional manner.

38. The device of claim 32, wherein the device comprises a V-shape.

39. An aqueous humor shunt device for implantation in a living eye having an anterior chamber and a Schlemm's canal for diverting aqueous humor from the anterior chamber into Schlemm's canal, the shunt device comprising:
a distal portion having at least one terminal aspect sized and shaped to be received circumferentially within a portion of Schlemm's canal and a proximal portion having at least one terminal aspect sized and shaped to be received within the anterior chamber,
wherein one or both of the proximal portion or the distal portion comprises an aqueous humor directing channel;
wherein the device permits fluid communication from the proximal portion in the anterior chamber to the distal portion in Schlemm's canal,
wherein the proximal portion of the shunt intersects the distal portion, and
wherein the distal portion branches in two opposite directions from the intersection with the proximal portion permitting fluid communication from the anterior chamber in either direction along Schlemm's canal.

40. The shunt device of claim 39, wherein the proximal portion of the shunt intersects the distal portion at about the midpoint of the length of the distal portion.

41. The shunt device of claim 39, wherein the distal portion comprises a lumen therethrough that directs the passage of fluid into Schlemm's canal.

42. The shunt device of claim 39, wherein the distal portion comprises a plurality of fenestrations that allow the passage of fluid into Schlemm's canal.

43. The shunt device of claim 39, wherein the proximal portion has a lumen therethrough that facilitates the passage of fluid into the distal portion of the shunt.

44. The shunt device of claim 39, wherein the proximal portion has two lumens therethrough that facilitate the passage of fluid into the distal portion of the shunt in opposite directions.

45. The shunt device of claim 39, wherein the proximal portion has a plurality of fenestrations therein that facilitate the passage of fluid into the distal portion of the shunt.

46. The shunt device of claim 43, wherein the lumen of the proximal portion communicates with one or more fenestrations.

47. An aqueous humor shunt device for use in a living eye having an anterior chamber and a Schlemm's canal for relieving intraocular pressure by facilitating drainage from the anterior chamber of the living eye into Schlemm's canal, the shunt device comprising:
a body formed of material of a size and shape adapted to facilitate the passage of aqueous humor from the anterior chamber to and within Schlemm's canal;

said body having a length and shape adapted to be at least partially circumferentially retained within a portion of Schlemm's canal to facilitate the passage of aqueous humor from the anterior chamber to Schlemm's canal;

said body comprising a proximal portion having at least one terminal aspect for placement within the anterior chamber and a distal portion having at least one terminal aspect for placement within Schlemm's canal;

wherein one or both of the proximal portion or the distal portion comprises an aqueous humor directing channel;

wherein the proximal portion intersects the distal portion and wherein the distal portion branches in two opposite directions from the intersection with the proximal portion permitting fluid communication in either direction along Schlemm's canal with the anterior chamber.

* * * * *